(12) United States Patent
Tao et al.

(10) Patent No.: US 7,058,243 B2
(45) Date of Patent: Jun. 6, 2006

(54) OPTICAL FIBER SENSOR HAVING A SOL-GEL FIBER CORE AND A METHOD OF MAKING

(75) Inventors: Shiquan Tao, Starkville, MS (US);
Rajeev Jindal, Starkville, MS (US);
Christopher Winstead, Starkville, MS (US); Jagdish P. Singh, Starkville, MS (US)

(73) Assignee: Mississippi State University, Mississippi State, MS (US)

( * ) Notice: Subject to any disclaimer, the term of this patent is extended or adjusted under 35 U.S.C. 154(b) by 478 days.

(21) Appl. No.: 10/046,731

(22) Filed: Jan. 17, 2002

(65) Prior Publication Data

US 2003/0133639 A1 Jul. 17, 2003

(51) Int. Cl.
*G02B 6/00* (2006.01)
*C03B 37/16* (2006.01)
*C03B 8/00* (2006.01)

(52) U.S. Cl. .................. 385/12; 385/123; 385/143; 65/17.2; 65/395; 65/393; 65/439; 65/440

(58) Field of Classification Search ............. 65/17.2, 65/2, 395, 393, 439, 440; 385/12, 123, 141–143; 436/527; 423/335

See application file for complete search history.

(56) References Cited

U.S. PATENT DOCUMENTS

| 4,680,049 A | * | 7/1987 | Onorato et al. ............. 65/395 |
| 5,249,251 A | | 9/1993 | Egalon et al. |
| 5,250,095 A | * | 10/1993 | Sigel et al. ............... 65/378 |
| 5,904,983 A | | 5/1999 | Chan et al. ................ 428/392 |
| 6,022,748 A | | 2/2000 | Charych et al. |
| 6,158,245 A | * | 12/2000 | Savant ................... 65/17.2 |

OTHER PUBLICATIONS

Grattan, et al., "Fiber Optic Sensor Technology: Introduction and Overview", Grattan, et al. (eds.), Optical Fiber Sensor Technology Fundamentals, Kluwer Academic Publishers, Dordrecht, 1-44 (2000).

MacCraith, et al., "Optical Fiber Chemical Sensor Systems and Devices", Optical Fiber Sensor Technology, vol. 4, Chemical and Environmental Sensing, Grattan, et al. (eds.), Kluwer Academic Publishers, Dordrecht, 15-112 (1998).

(Continued)

*Primary Examiner*—Frank G. Font
*Assistant Examiner*—Michael P. Mooney
(74) *Attorney, Agent, or Firm*—DLA Piper Rudnick; Gray Cary US LLP (57) ABSTRACT

A simple, economic wet chemical procedure is described for making sol-gel fibers. The sol-gel fibers made from this process are transparent to ultraviolet, visible and near infrared light. Light can be guided in these fibers by using an organic polymer as a fiber cladding. Alternatively, air can be used as a low refractive index medium. The sol-gel fibers have a micro pore structure which allows molecules to diffuse into the fiber core from the surrounding environment. Chemical and biochemical reagents can be doped into the fiber core. The sol-gel fiber can be used as a transducer for constructing an optical fiber sensor. The optical fiber sensor having an active sol-gel fiber core is more sensitive than conventional evanescent wave absorption based optical fiber sensors.

49 Claims, 9 Drawing Sheets

OTHER PUBLICATIONS

"Applications", Chemical and Biochemical Sensing with Optical Fibers and Waveguides, Part IV, Boisdé, et al. (eds.), Artech House Inc, Boston, 285-289 and 339-353 (1996).

Messica, et al., "Theory of Fiber-Optic, Evanescent-Wave Spectroscopy and Sensors", Applied Optics, 35, 13, 2274-2284 (1996).

Badini, et al., "Sol-Gels with Fiber Optic Chemical Sensor Potential: Effects of Preparation, Aging, and Long-Term Storage", Rev. Sci. Instrum., 66, 8, 4034-4040 (1995).

MacCraith, et al., "Sol-Gel Coatings for Optical Chemical Sensors and Biosensors", Sensors and Actuators, B29, 51-57 (1995).

Flora, et al., "Comparison of Formats for the Development of Fiber-Optic Biosensors Utilizing Sol-Gel Derived Materials Entrapping Fluorescently-Labelled Proteins", Analyst, 124, 1455-1462 (1999).

Keeling-Tucker, et al., "Controlling the Material Properties and Biological Activity of Lipase Within Sol-Gel Derived Bioglasses Via Organosilane and Polymer Doping", Chemistry of Materials, 12, 3695-3704 (2000).

Yan, et al., "Synthesis, Characterizations, and Optical Properties of Stacked Porous Thin Film Derived from Sol-Gel Process", J. Am. Ceram. Soc., 79, 4, 1061-1065 (1996).

Santos, et al., "Properties of Porous Silica Glasses Prepared Via Sol-Gel Process", Journal of Non-Crystalline Solids, 273, 145-149 (2000).

Tanaka, et al., "Monolithic LC Column: A New Type of Chromatographic Support Could Lead to Higher Separation Efficiencies", Anal. Chem., 73, 420A-429A (2001).

Hypszer, et al., "Fiber Optic Technique for Relative Humidity Sensors", SPIE, 3054, 145-150 (1997).

* cited by examiner

OPTICAL FIBER SENSOR HAVING A SOL-GEL FIBER CORE AND A METHOD OF MAKING

This invention was made with U.S. Government support under Contract No. DE-FC26-98FT-40395 awarded by the Department of Energy. The U.S. Government may have certain rights in this invention.

BACKGROUND OF THE INVENTION

1. Field of the Invention

This invention relates generally to the field of optical fiber sensors and, in particular, to the fabrication of porous sol-gel optical fibers, implantation of sensing materials for chemical and biochemical sensing in the sol-gel fibers, and the manufacture of optical fiber sensors therefrom.

2. Background of the Technology

Optical fiber chemical and biochemical sensors are based on detecting the interaction of a chemical or biochemical component with light guided by an optical fiber. See, for example, "Optical Fiber Sensor Technology: Fundamentals", Grattan and Meggitt, eds., Kluwer Academic Publishers, Dordrecht (2000). These sensors can be used for environmental monitoring, chemical process control, and biochemical sensing. See, for example, "Optical Fiber Sensor Technology", Volume 4: Chemical and Environmental Sensing", Grattan and Meggitt, eds., Kluwer Academic Publishers, Dordrecht (1999) and "Chemical and Biochemical Sensing with Optical Fibers and Waveguides", Boisd and Harmer, eds., Artech House Inc., Boston (1996). Compared with other sensors, such as electrochemical sensors, surface acoustic wave sensors, optical fiber sensors have the following advantages for chemical and biochemical sensing: small size, low cost, fast response, remote and distributed sensing capability, resistance to severe environments, and immunity to electrical noise.

According to the structure of the sensor transducer, two kinds of optical fiber sensors can be defined. In the first class of optical fiber sensor, the optical fiber itself is not a transducer. The transducer is a conventional optical cell used in spectrometry. The transducer can be a quartz cell filled with solution, a drop of aqueous solution, a small piece of porous polymer or a polymer film. In this type of sensor, an optical fiber is used to send light from a light source into the transducer and guide light from the transducer to a light detector. This kind of optical fiber sensor, however, is both insensitive and susceptible to noise from its environment. When a light beam from an optical fiber is guided to a traditional optical cell the light beam is highly diffused while traveling through the cell. Even with an efficient light collecting system the path length of the transducer still has to be limited. In addition, noise light signals from the environment are also collected and fed into the detector.

In the second class of optical fiber sensor, the cladding of the optical fiber itself can act as a transducer. A sensor of this type is disclosed by Mesica et al. in "Theory of Fiber-Optic, Evanescent-Wave Spectroscopy and Sensors", Appl. Optics, 35, 2274 (1996). In order to manufacture such a sensor, the jacket and cladding of a conventional optical fiber are removed and a sensing material is coated on the surface of the fiber core to form a film which serves as a new cladding layer. The evanescent tail of the light guided in the fiber interacts with the sensing material in the cladding layer to yield a sensing signal. This kind of optical fiber sensor has the advantages of simple structure and immunity to environmental noise. However, the sensitivity of this kind of sensor is still limited since only a small part of the light guided through the optical fiber interacts with the sensing material. Moreover, only the sensing material within the evanescent wave field (e.g., within several micro-meters from the fiber core surface) is effective for sensing.

A significant increase in sensitivity would be expected if the fiber core rather than the cladding were used as the sensing material. Using such an active fiber core sensor, almost all of the light guided through the fiber would interact with the sensing material. In addition, since the probing light is guided within the optical fiber as it travels through the active fiber core, the problem of diffusion of the light beam is avoided and a very long active fiber core can be used as a sample cell. Also, the effect of light noise from the environment of the sensor could be avoided.

U.S. Pat. No. 5,249,251 discloses sensors having an active fiber core for fluorescence or chemiluminescence detection. U.S. Pat. No. 5,250,095 discloses a high temperature/wet chemistry procedure to make porous optical fibers. The porous optical fibers can be used as chemical sensors. The '095 patent discloses drawing a glass rod to form a fiber, treating a portion of the glass fiber to induce phase separation of the glass components and dissolving soluble components of the glass to make that portion of the fiber porous. The porous part of the fiber is then dipped in a solution to adsorb sensing material into the micro-pore in the fiber.

There still exists a need for a simple, economic and convenient method to make a porous, transparent fiber. Such a porous fiber could be used to make an optical fiber sensor by implanting a sensing material into the porous fiber.

Other objects and advantages of this invention are apparent from the specifications and drawings which follow. The application of the porous sol-gel fiber sensor is considerably broader than its use discussed herein as examples.

SUMMARY OF THE INVENTION

According to a first aspect of the invention, a method for making a porous sol-gel fiber is provided. The method includes hydrolyzing a silicate ester with water using a catalyst to form a hydrolyzed solution, transferring the hydrolyzed solution into the cavity of a mold, allowing the hydrolyzed solution to gelatinize to form a sol-gel fiber, removing the sol-gel fiber from the mold, and allowing the sol-gel fiber to dry. The catalyst can be an acid catalyst (e.g., a mineral acid) or a base catalyst. According to a preferred embodiment of the invention, the method also involves incorporating a sensing material into the sol-gel fiber. A method for constructing an optical fiber sensor is also provided wherein the sol-gel fiber is positioned between a light source and a light detector such that light from the light source passes through the sol-gel fiber and impinges on the light detector.

According to a second aspect of the invention, an optical fiber sensor is provided. The optical fiber sensor includes a light source, a light detector, and a transducer. The transducer comprises a porous fiber core made by a sol-gel method as set forth above wherein the sol-gel fiber has a sensing material incorporated therein. Light from the light source passes through the transducer and impinges on the light detector. The optical fiber sensor as set forth above can further include a lens positioned between the light source and the transducer such that light from the light source is focused by the lens before passing through the transducer. The optical fiber sensor can also include a first optical fiber positioned between the lens and the transducer and a second optical fiber positioned between the transducer and the light detector. The optical fiber sensor may also include a data acquisition system in communication with the light detector.

The transducer in the aforementioned optical fiber sensor can be positioned inside a chamber which, according to a preferred embodiment of the invention, can include an inlet and an outlet such that a sample fluid flowing into the chamber through the inlet contacts the surface of the transducer and exits the chamber through the outlet. According to a further preferred embodiment of the invention, the first optical fiber can pass through a first opening in the chamber and can be optically coupled to a first end of the transducer inside the chamber and the second optical fiber can pass through a second opening in the chamber and be optically coupled to a second end of the transducer inside the chamber.

According to a third aspect of the invention, a method for determining the concentration of an analyte in a sample fluid using a sensor as set forth above is provided. The method includes steps of contacting the transducer with the sample fluid and monitoring the signal from the light detector while directing light through the transducer. The signal from the light detector can be compared to a calibration curve to determine the amount of analyte in the sample. The calibration curve can be generated by contacting a plurality of fluid samples having known concentrations of analyte with the transducer and monitoring the signal from the light detector while directing light through the transducer to generate a set of data points. A curve can then be fit to the data points to generate the calibration curve.

According to a fourth aspect of the invention, an optical fiber transducer having a porous fiber core made by a sol-gel method as set forth above is provided. The transducer may be doped with a sensing material. The optical fiber transducer can further include a cladding material disposed on the core.

According to a fifth aspect of the invention, an optical fiber sensor including a light detector and a transducer in optical communication with the light detector is provided. The sensor may also include a light source oriented such that light from the light source impinges on the transducer. According to this aspect of the invention, light generated inside the transducer (e.g., by fluorescence or chemiluminescence) impinges on the light detector. The transducer comprises a sol-gel fiber as set forth above wherein a sensing material is incorporated into the sol-gel fiber.

A method for determining the presence or concentration of an analyte in a sample fluid using the aforementioned sensor is also provided. The method includes contacting the transducer with the sample fluid and monitoring the signal from the light detector. Light from the light source may be impinged on the surface of the transducer during monitoring.

BRIEF DESCRIPTION OF THE FIGURES

The invention will be described with reference to the accompanying figures, wherein.

DETAILED DESCRIPTION OF THE INVENTION

The present invention provides a method of making porous sol-gel fibers. The method according to the invention also comprises implanting a sensing material into the sol-gel fiber and constructing optical fiber sensors using the sol-gel fiber as a transducer.

According to the invention, a sol-gel process is used to make porous sol-gel fibers. The physical properties of the sol-gel fiber, such as the porosity, pore size, and the fiber dimension (e.g., fiber diameter and length) can be controlled by controlling the sol-gel composition, the gelatinizing conditions and the size of the fiber mold. The chemical composition of the sol-gel fiber can be adjusted according to the application purpose of the sensor.

The present inventors have discovered that the optical properties and structural characteristics of fibers made using a sol-gel process are particularly suitable for use as transducers in an optical fiber sensor. An optical fiber sensor according to the invention can comprise a porous sol-gel fiber as the transducer, an optional light source, and a light detector. An optical fiber can also be used to transmit light from the light source to the transducer and another optical fiber can be used to transmit light from the transducer to the light detector. In certain applications, a dispersing element or an optical filter can also be employed in the sensor to select light of a specific wavelength or range of wavelengths.

According to the invention, a porous sol-gel fiber that does not have a sensing material incorporated therein can be used as an optical cell for intrinsic optical detection. The light absorption or emission, (e.g., fluorescence, chemiluminescence etc.) of some species can be directly detected with an intrinsic optical fiber sensor of this type.

When a sensing material is incorporated into the sol-gel fiber, the sensing material can interact with an optically inert analyte to produce an optical signal (e.g., by absorption, fluorescence, or chemiluminescence). For example, the sensing material can react with the analyte to form a complex. This complex can then produce an optical signal (e.g., by chemiluminescence) which can be detected to indicate the presence and/or the amount of the analyte. The optical signal can also originate from the colliding of analyte molecules with molecules of the sensing material (e.g., fluorescence).

The sensing material according to the invention can be incorporated into the sol-gel fiber during the fiber manufacturing process. The sensing material can also be absorbed on the surface of micro pores within the porous fiber by soaking the fiber in an appropriate chemical solution.

The fiber containing the sensing material can also acts as a reaction medium wherein components from the surrounding environment can diffuse into the fiber core and react with the sensing material to produce a sensing signal. In addition, the sol-gel fiber, either with or without a sensing material, can be used as a pre-concentrator to concentrate material from the surrounding environment for detection. Moreover, the porous sol-gel fiber can also act as a filter to separate interference material from a sample fluid. For example, the porous sol-gel fiber can be used as a filter in biochemical or clinical applications (e.g., in blood and urine analysis, to separate large molecules from small molecules, etc.).

Figure 1A:
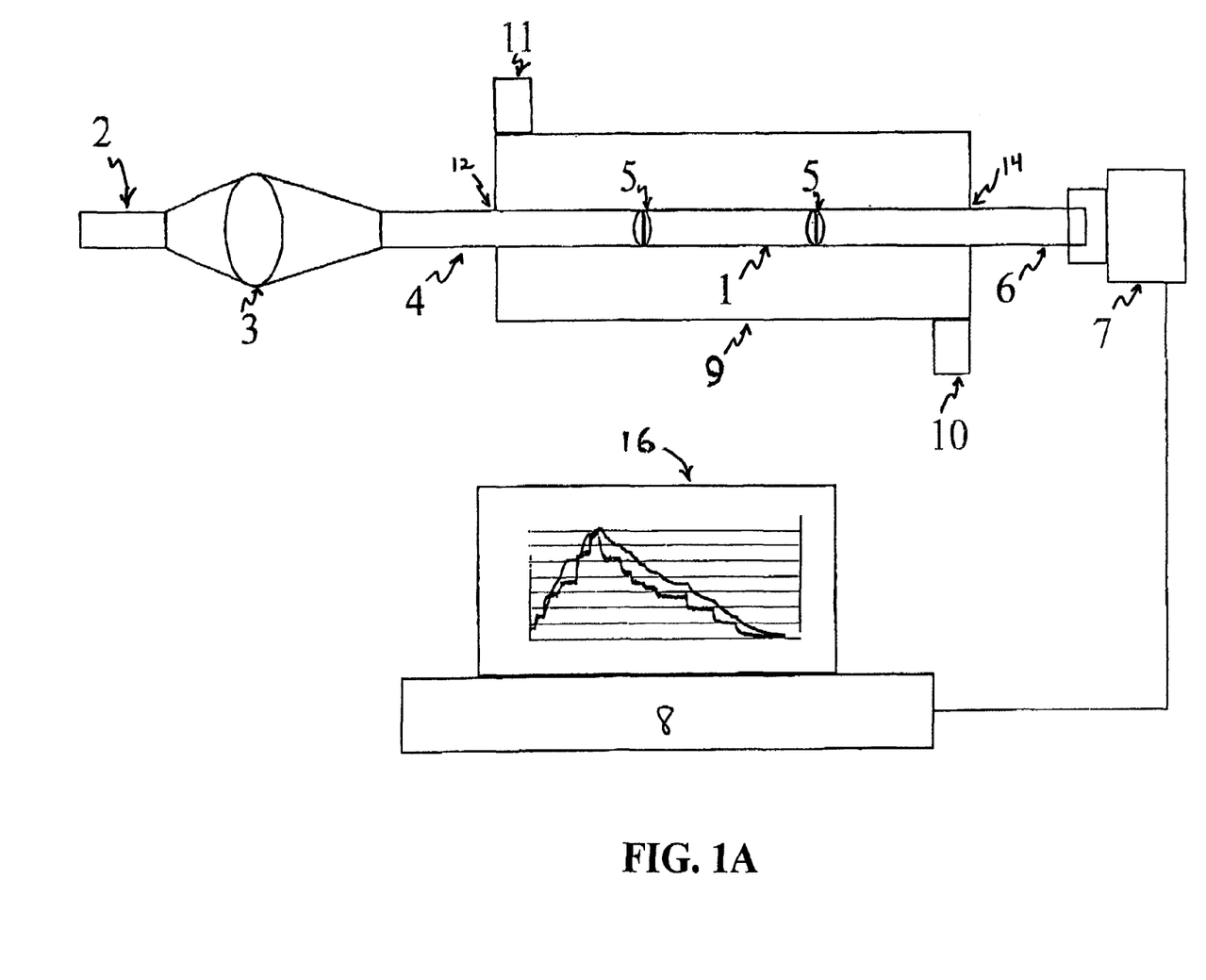
FIG. 1A is a schematic showing a first embodiment of an optical fiber sensor according to the invention wherein the light source is oriented to direct light along the length of the transducer.

FIG. 1A shows the structure of optical fiber sensor using an active sol-gel fiber core as a transducer. The optical fiber sensor comprises a transducer 1 which, according to the invention, is a porous sol-gel fiber doped with a sensing material. The sensor also comprises light source 2 and lens 3 to focus light into an optical fiber 4. Optical fiber 4 can be connected to transducer 1 by optical coupling 5. According to a preferred embodiment of the invention, an optically transparent adhesive can be used to couple transducer 1 to optical fiber 4. As shown, optical fiber 6 can be used to guide light from transducer 1 to light detector 7. Optical fiber 6 can also be connected to transducer 1 by optical coupling 5. The transducer 1 is shown mounted in a chamber 9 with inlet and outlet ports 10, 11. Inlet and outlet ports 10, 11 allow a sample fluid containing an analyte to flow through the chamber. Optical fiber 4 passes through first opening 12 in chamber 9 and optical fiber 6 passes through second opening 14 in chamber 9. In this manner, transducer 1 can be enclosed by chamber 9.

The sensor shown in FIG. 1A and described above is merely exemplary of a sensor according to the invention and is not intended to be limiting. Sensors having other configurations are also possible. For example, one of the optical fibers 4, 6 in FIG. 1 can be bent back upon itself and formed into a "U" shape. In this manner, the light source and the detector can be arranged on the same side by using the "U" shaped fiber to guide the light. This arrangement can be used to provide a sensor which is more compact. For some specific applications the fibers 4 and 6 can be connected to the transducer through melting using a laser (e.g., a $CO_2$ laser) or using other known heating techniques. In another compact design, optical fibers 4, 6 can be omitted. Light from a light source can be directly focused into the sol-gel fiber and the detector can be placed directly behind the sol-gel fiber. In practical use of the sensor for monitoring or detecting an analyte, the chamber 9 can be omitted and the transducer can be inserted directly into the sample fluid. For purposes of the invention, the transducer will be considered to be positioned between the light source and the light detector in any arrangement wherein light from the light source can be transmitted through the transducer and impinge upon the light detector including the arrangement wherein the light source and the light detector are arranged on the same side of the transducer.

As shown in FIG. 1, data acquisition system 8 in communication with light detector 7 can be used to continuously monitor the sensor signal. Data acquisition system 8 can comprise a computer for analyzing the signal data from light detector 7 as well as monitor 16 for displaying the collected data in a suitable format.

Light source 2 can be a line source (e.g., a laser or a mercury lamp), a band source (e.g., a light emitting diode), or a continuous light source (e.g., a tungsten lamp, a deuteron lamp or a tungsten halogen lamp, etc.) coupled with a monochromator or a band-pass filter.

Optical fibers 4, 6 can be made of glass (e.g., silica) or plastic. The type of fiber can be chosen based upon the wavelength of the light used for the specific application. Light detector 7 can be, for example, a photodiode, a photomultiplier tube (PMT) or a charge-coupled detector (CCD). The sensor structure illustrated in FIG. 1 can be used for both light absorption and fluorescence detection.

Figure 1B:
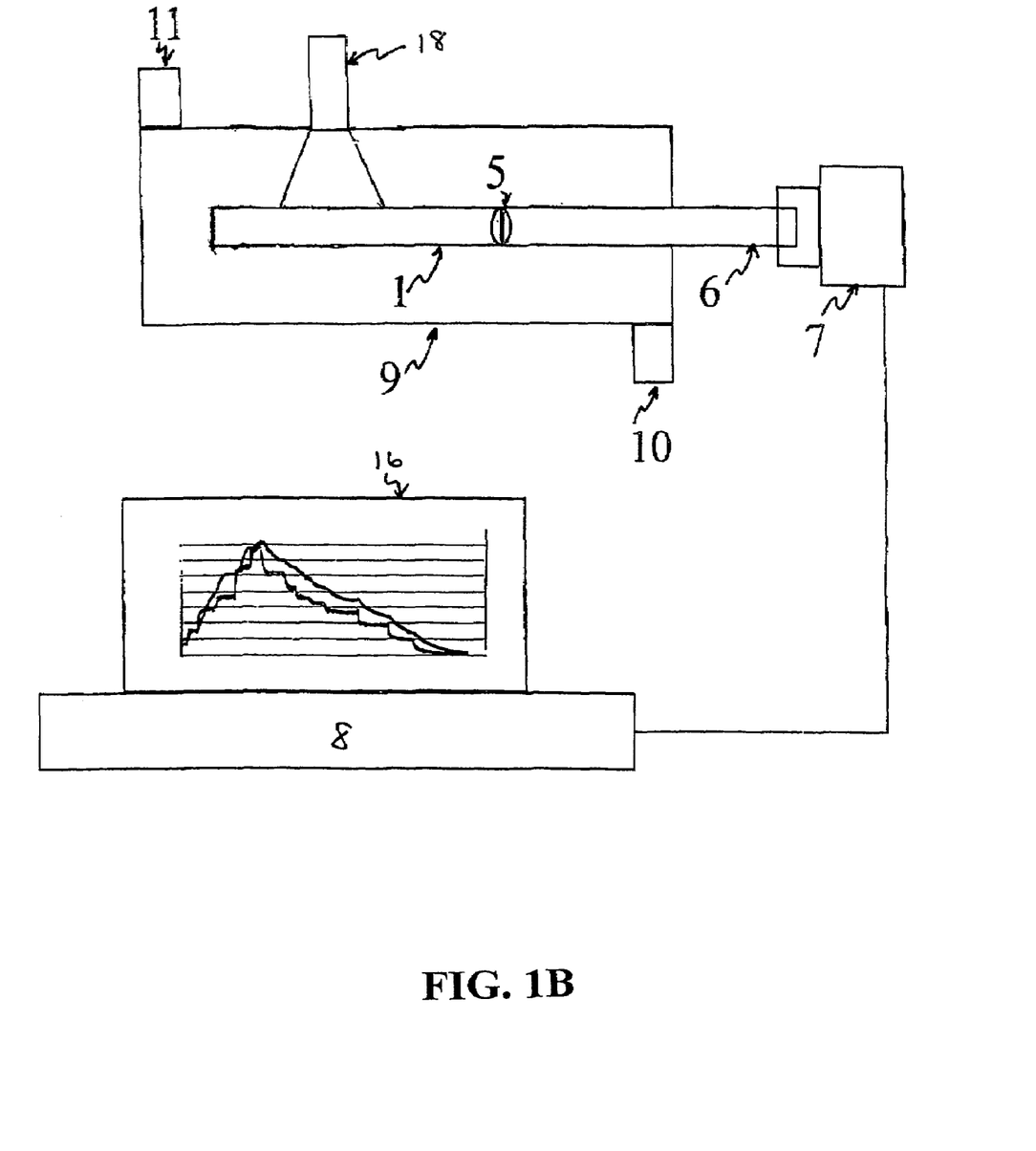
FIG. 1B is a schematic showing a second embodiment of an optical fiber sensor according to the invention wherein the light source is oriented transverse to the transducer.

According to a further embodiment of the invention, the light source, rather than directing light along the length of the sensor as is shown in FIG. 1A, can instead direct light at an angle to the length of the sensor to impinge on exposed surfaces of the transducer. This arrangement, which is depicted in FIG. 1B, can be used according to the invention for fluorescence detection. As can be seen in FIG. 1B, light from transverse light source 18 impinges on the surface of transducer 1. Fluorescent emissions generated inside the transducer can then be directed by transducer 1 and optical fiber 6 to impinge on light detector 7. Light source 18 is shown oriented at a right angle (i.e., 90 degrees) to the length dimension of transducer 1. However, light source 18 can be oriented at angles other than 90 degrees to the length dimension of transducer 1. When light is generated inside the transducer by chemiluminescent emissions, light source 18 is not required and can be omitted.

Figure 2A:
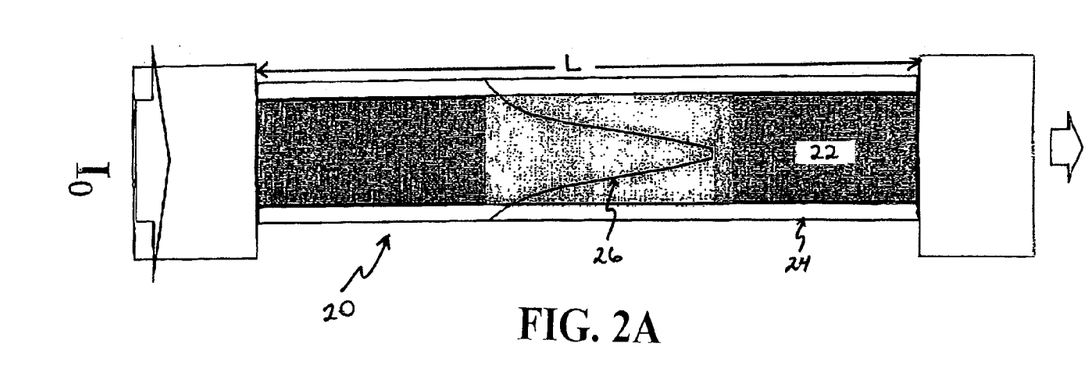
FIG. 2A shows the light intensity distribution of a light beam guided through an optical fiber transducer having an active fiber core according to the present invention.
Figure 2B:
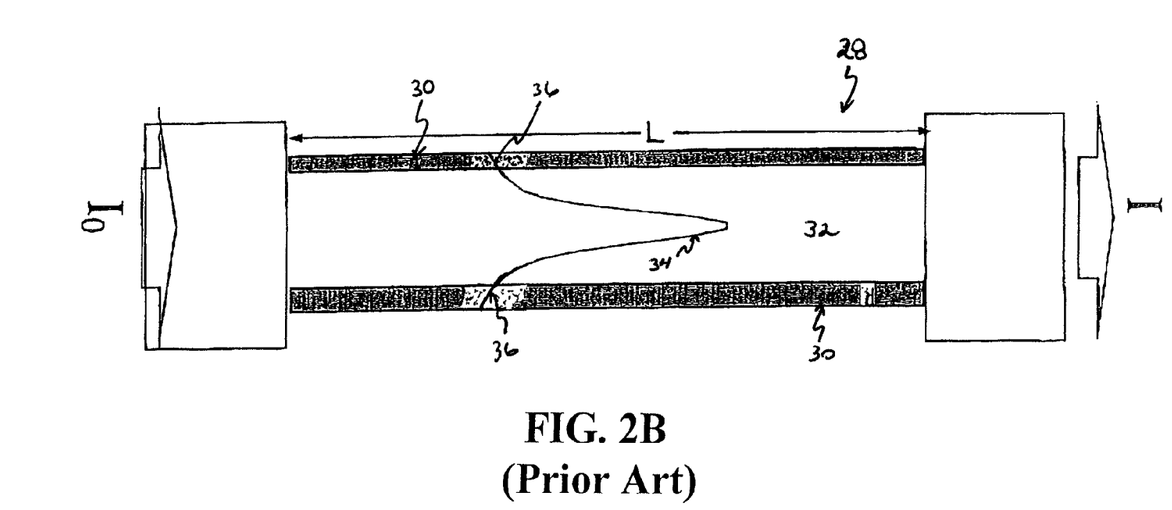
FIG. 2B shows the light intensity distribution of a light beam guided through an optical fiber transducer having an active film cladding according to the prior art.

In FIGS. 2A and 2B show light intensity distribution of a light beam guided through an optical fiber transducer having an active fiber core according to the invention and an active fiber cladding, respectively. In particular, FIG. 2(A) shows a cross sectional view of an optical fiber transducer 20 with an active fiber core 22 according to the invention. A cladding 24 is shown on active fiber core 22. The cladding can be a separate material provided on the surface of the active fiber core 22. Alternatively, air can be used as a cladding. Incident light is represented by $I_0$ and light transmitted through transducer 20 is represented by I. Light intensity distribution 26 is also represented in FIG. 2A. Using this arrangement, almost all of the light guided through the fiber interacts with sensing material in the fiber core. In addition, the pass length of the sample cell (i.e., the active fiber core) can be very long.

FIG. 2(B) shows a cross-sectional view of a prior art optical fiber sensor 28 comprising an active film or cladding 30 coated onto the surface of a fiber core 32. As in FIG. 2A above, incident light is represented by $I_0$ and light transmitted through transducer 28 is represented by I. Light intensity distribution 34 is also represented in FIG. 2B. In this case, only a small portion 36 (i.e., the evanescent tail) of the light guided through the fiber interacts with sensing material in the active cladding 30. Also, the evanescent wave can only reach a very short distance (typically measured in μm) from the surface of fiber core 32. Therefore, the actual volume of the sample cell is limited.

Taking light absorption as an example, the sensor signal for an optical fiber transducer with an active fiber core (FIG. 2A) and an optical fiber transducer with an active coating film (FIG. 2B) are set forth below.

For active fiber core transducers according to the invention:

$$A = \log(I_0/I) = 0.434\ kCL$$

wherein k is the absorption coefficient, C is the concentration of light absorber and L is the length of the active fiber core.

For active fiber cladding transducers:

$$A = \log(I_0/I) = 0.434 \, rkC(2d)L$$

wherein $r = (n_c/n_f)f$ and $n_c$ and $n_f$ are the refractive index of the fiber core and the film coating, respectively and f is the fraction of total power that interacts with the absorber in coating layer. The value of the variable f is usually less than 0.1. The variable d in the above formula is the thickness of the coating. The thickness of the coating layer is usually in the µm range, which is typically much smaller than the light path length L which, for example, can be from one centimeter to several meters.

Comparing the above two equations, it is clear that an optical fiber sensor with an active fiber core according to the invention can have a much higher sensitivity than an optical fiber sensor with active film coating.

To make an active fiber core for an optical fiber sensor the material chosen to make the fiber core should preferably possess certain properties. These properties include: high transparency to the light used for sensing; the ability to trap or absorb sensing material; and the ability to be formed into a fiber. Moreover, the material used as the active fiber core should allow the material being sensed to diffuse into the fiber core. Furthermore, the material should be inert under the test conditions employed. The ability of the material to withstand high temperature or very cold environments is also useful in some specific applications according to the invention.

Porous sol-gel glass can be used according to the invention to make the fiber core. Porous sol-gel glass has been used as a coating material for active film coated optical fiber sensors. See, for example, Badini, et al., "Sol-Gels with Fiber Optic Chemical Sensor Potential: Effects of Preparation, Aging, and Long-Term Storage", Rev. Sci. Instrum., 66, 4034 (1995). See also MacCraith, et al., "Sol-Gel Coatings for Optical Chemical Sensors and Biosensors", Sensors and Actuators, B29, 51 (1995); Flora et al., "Comparison of Formats for the Development of Fiber-Optic Biosensors Utilizing Sol-Gel Derived Materials Entrapping Fluorescently-Labelled Proteins", Analyst, 124, 1455 (1999); and Keeling-Tucker et al., "Control of the Material Properties and Biological Activity of Lipase within Sol-Gel Derived Bioglasses via Organosilane and Polymer Doping", Chemistry of Materials, 12, 3695 (2000). The aforementioned references disclose coating a sol-gel film onto a silica fiber surface and doping chemical and biochemical reagents into the sol-gel film. As disclosed in U.S. Pat. No. 6,022,748, even macro hydrophobic bio-molecules, such as enzymes, antigens and viruses, can also be trapped in the sol-gel film through addition of specific reagents. These doping techniques can be used to dope sensing materials into the sol-gel fiber core according to the invention.

According to the invention, a porous sol-gel glass fiber can be made by mixing a silicate ester, such as tetramethyl orthosilicate (TMOS) or tetraethyl orthosilicate (TEOS), with water in the presence of a catalyst. According to a preferred embodiment of the invention, the catalyst is a mineral acid such as hydrochloric or sulfuric acid. However, any catalyst for hydrolysis can be used according to the invention including acid catalysts and base catalysts. The clear solution obtained from hydrolysis can then be transferred into the cavity of a mold for gelatinization. According to a preferred embodiment of the invention, the mold is a tubular cavity. After the sol-gel material has sufficiently gelatinized, the sol-gel fiber is removed from the mold. The resulting fiber is then allowed to dry before use. According to a preferred embodiment of the invention, the fiber is allowed to air dry. The air dry time typically ranges from 3 to 4 hours. Other types of drying including forced air drying and drying at elevated temperatures could also be used according to the invention.

The basic chemical composition of sol-gel glass is $SiO_2$, which is the same as that of quartz. This material is essentially transparent to ultraviolet, visible, infrared light. See, for example, Yan et al., "Synthesis, Characterizations, and Optical Properties of Stacked Porous Thin Film Derived from Sol-Gel Process", J. Am. Ceram. Soc., 79, 1061 (1996). These properties make the sol-gel material particularly useful for constructing an optical sensor. Various small molecules such as $H_2O$, $CH_3OH$, $C_2H_5OH$ which can exist in the porous structure of the sol-gel glass. These small molecules, which can be formed during hydrolysis of the orthosilicate ester, can become trapped in the micro porous structure of the sol-gel glass during the gelatinization process. These molecules, especially the organic species, can absorb ultraviolet light and can interfere with optical sensing in some cases. However, these materials can be driven out of the glass by flowing a high purity gas (e.g., air, nitrogen or argon gas) through the porous glass.

Depending upon the application of the sensor, the chemical composition of the sol-gel fiber can be tailored by doping appropriate chemicals, biochemical reagents or biochemically active materials, such as enzymes or bacteria, into the sol-gel fiber as sensing materials. This ability to tailor the composition of the sol-gel fiber allows the fiber to be used to make sensors for a variety of different applications.

In order to incorporate the sensing material into the fiber, the sensing material can be added to the water used for the hydrolysis of the silicate ester. The sensing material can also be added to the sol-gel solution obtained from hydrolysis. The concentration of sensing material in the sol-gel fiber can be varied depending upon the desired sensitivity of the optical fiber sensor according to the invention. A higher concentration of sensing material in the sol-gel fiber can increase the sensitivity of the sensor in some cases. However, too much doping can make the fiber fragile. Also, the optical properties of the fiber can be affected when there is too much sensing material in the sol-gel fiber. The amount of sensing material that can be incorporated into the sol-gel fiber can depend upon the properties of the sensing material as well as the properties of the sol-gel glass (e.g., the sol-gel glass microstructure, etc.).

Another method of incorporating sensing material into the sol-gel fiber is to dip the fiber into a specific solution to absorb the solution into the micro porous structure of the sol-gel fiber. After removing the solvent, the solute can remain deposited in the pores of the sol-gel glass. Fiber doped in this way can be used, for example, for sensing gaseous samples.

The micro-porous structure of the sol-gel glass provides desirable characteristics for optical fiber sensor applications. First, the micro-porous structure allows molecules from the surrounding environment to diffuse into the glass fiber where they can interact with the sensing material. Second, the micro-porous structure allows reagents to be absorbed into the fiber for sensing purposes. Furthermore, the porosity and pore size of the sol-gel fiber can influence the response time of the sensor. The pore size of a sol-gel fiber can, for example, range from nano-meters to micro-meters, and the porosity can range from several percent up to 50%. See, for example, Santos et al., "Properties of Porous Silica Glasses Prepared via Sol-Gel Process", J. Non-Crystalline Solid, 273, 145 (2000) and Tanaka, et al.,"Monolithic LC Column: A New Type of Chromatographic Support Could Lead to Higher Separation Efficiencies", Anal. Chem., 73, 420A (2001). The factors affecting the micro-porous structure and porosity of sol-gel glass can include the original silicate ester composition, the ratio of water to silicate, the solution composition of hydrolyzed silicate, the gelation time and temperature etc. Any of these variable can be adjusted according to the invention to provide a sensor having desirable properties for a particular application.

The fiber diameter can also influence the response time of optical fiber sensors having an active fiber core according to the invention. With a smaller fiber diameter, analyte molecules can diffuse into the fiber in a shorter time. The response time of the optical fiber is proportional to $1/r^2$ where r is the radius of the fiber. Therefore, a small diameter fiber can be used when a fast response sensor is required. Additionally, the efficiency of light coupled into the fiber from the light source is smaller when a smaller optical fiber is used. Therefore, for smaller diameter fibers, a stronger light source (e.g., a laser) and/or a more sensitive light detecting element (e.g., a photomultiplier tube) could be used.

In the optical fiber sensor according to the invention, higher sensitivities can be obtained by using a longer sol-gel fiber. The length of sol-gel fiber that can be made according to the invention is preferably from one centimeter up to several centimeters in length. Longer sol-gel fibers, however, can be difficult to make due to cracks formed in the fiber during the gelatinizing process. However, if an organic film forming polymer (e.g., polyvinyl alcohol) is added to the sol-gel solution, a longer fiber can be obtained. A sol-gel fiber containing an organic polymer can also be less fragile and easier to handle.

A sol-gel glass fiber having a diameter of 200 µm was constructed using a 250 µm Tygon® tube as a mold. Tygon® is a registered trademark of Norton Corporation of Worcester, Mass. Smaller or larger tubes, however, can also be used to create smaller or larger fibers according to the invention.

EXAMPLE 1

Moisture Sensor

A sol-gel fiber sensor for moisture sensing was constructed by using a cobalt chloride ($CoCl_2$) doped sol-gel fiber as a transducer. $CoCl_2$ is a solid material that is normally blue in color. $CoCl_2$, however, reacts with water molecules to form a complex, $Co(H_2O)_6Cl_2$ which is pink in color. This property makes the compound useful as an indicator for a desiccating agent such as silica gel. The water molecule concentration in a sample (e.g., moisture content of a gas or liquid phase) can be quantitatively determined with spectrometric detection of the light absorption by $CoCl_2$ (peak absorption at 690 nm) or the absorption signal of its water molecule coordinated complex (peak absorption at 500 nm).

A porous sol-gel fiber for constructing a moisture sensor was obtained by the following procedure. Solid cobalt chloride was dissolved in water. The $CoCl_2$ containing water was used for hydrolyzing tetramethyl orthosilicate (TMOS). The TMOS was mixed with $CoCl_2$ containing water in presence of trace hydrochloric acid for several minutes. The clear solution obtained was filled into a Tygon tube and allowed to gelatinize in the tube for one week. The sol-gel fiber was then pushed out of the tube and air-dried. A $CoCl_2$-doped sol-gel fiber was cut and was used to construct an optical fiber sensor as described above. The light source for the sensor is a He—Ne laser with wavelength of 630 nm. A photodiode was used as the detector. The $CoCl_2$ concentration in the sol-gel fiber and the length of the fiber used to construct the sensor was chosen according to the moisture content range to be sensed. Since $CoCl_2$ absorbs light of 630 nm from the light source, a high concentration of $CoCl_2$ doped into the sol-gel fiber is better for high moisture content sensing. A low concentration of $CoCl_2$ doped into the sol-gel fiber provides better results when sensing low moisture content.

The moisture transducer was set in a small plastic chamber having inlet and outlet ports for a sample gas. A commercial moisture sensor based on the detection of capacitance inside the sensor chamber was used to monitor the moisture content in the test chamber during the test. Compressed air with a relative humidity of about 15% was divided into two flow lines. One flow line passed through a desiccant (anhydrous calcium sulfate) filled column. The gas flowing out of this column was therefore dried. The sample gas flow was obtained by mixing the dry air with moisture containing air from the second flow line. Varying the ratio of the two gases varied the moisture content of the sample.

Figure 3:
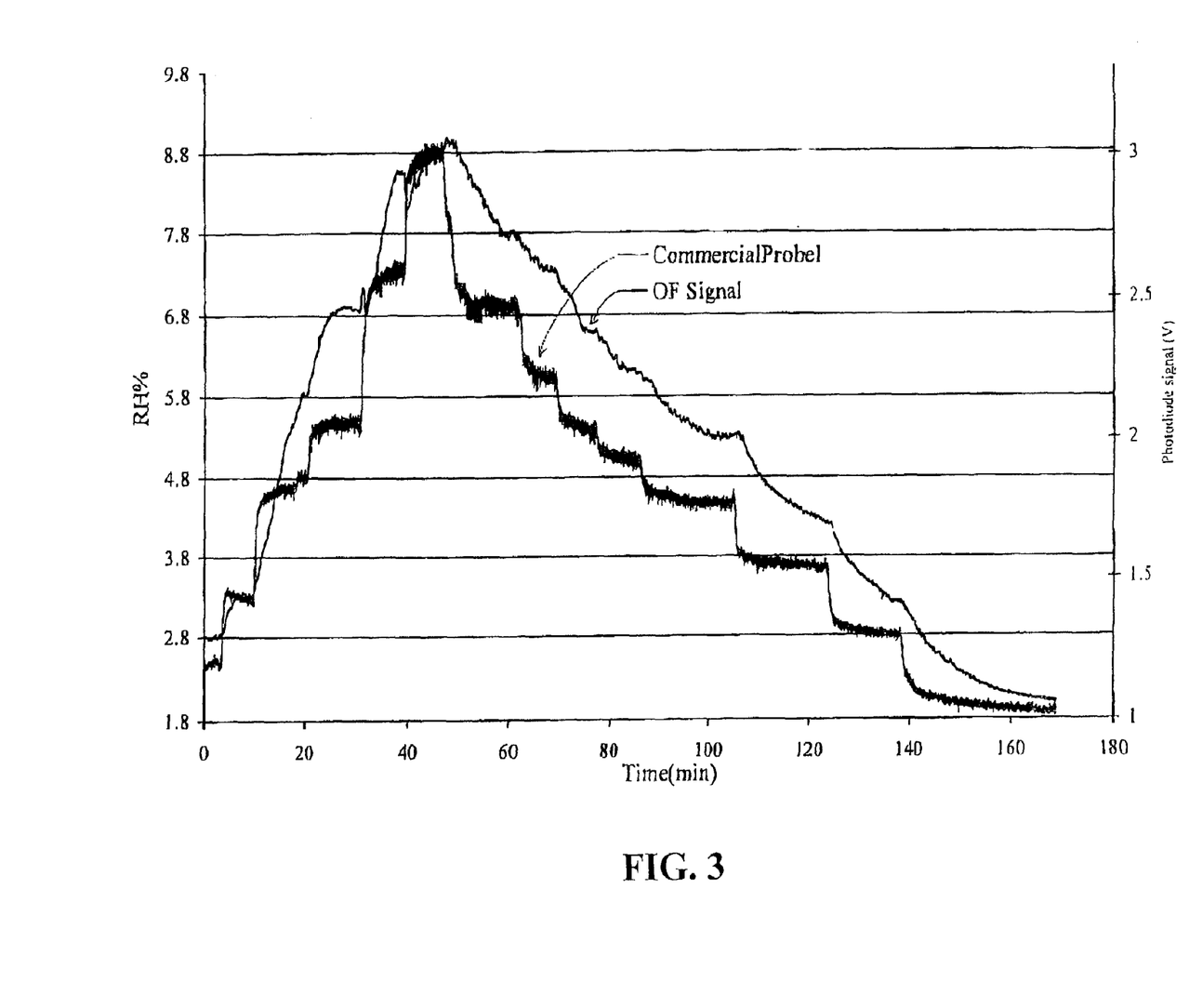
FIG. 3 shows the output signal from a photodiode as a function of time for a first moisture sensor according to the invention.

FIG. 3 shows the test results for a first moisture sensor comprising a $CoCl_2$ doped sol-gel fiber. FIG. 3 shows the relative humidity (RH %) as measured by a commercial moisture probe and the photodiode signal generated by a moisture sensor according to the invention as a function of time in minutes. The relative humidity in the chamber was varied in steps and the signal generated by the moisture sensor was measured. The $CoCl_2$ concentration in the sol-gel fiber transducer used in the experiment was 2%, the length of the sol-gel fiber transducer was 2 mm and the diameter of the fiber transducer was approximately 400 µm. As can be seen from FIG. 3, this sensor was capable of detecting moisture contents of less than 2% relative humidity, which is below the detection limit of the commercial moisture sensor.

Figure 4:
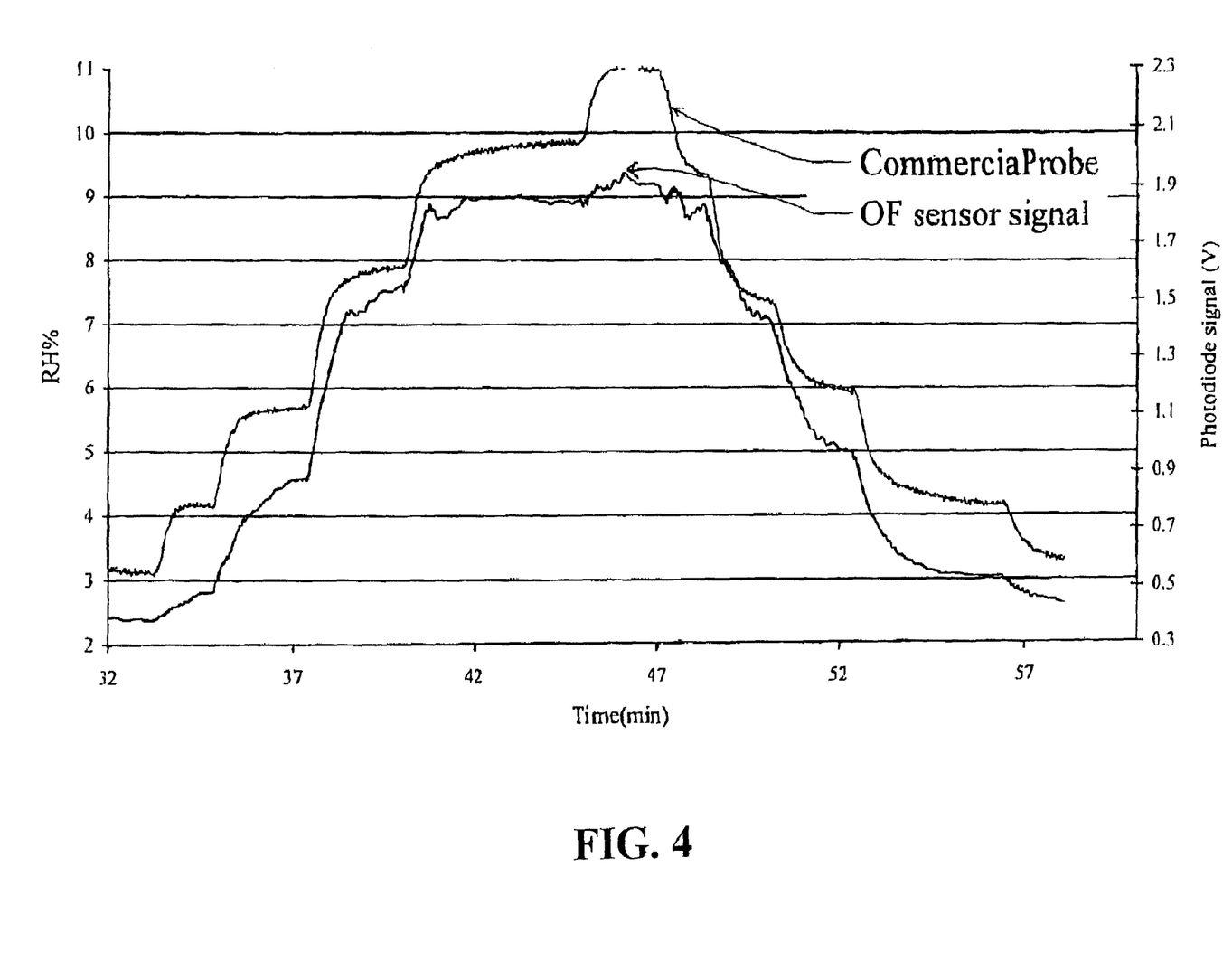
FIG. 4 shows the output signal from a photodiode as a function of time for a second moisture sensor according to the invention.

FIG. 4 shows the time response of a second sol-gel fiber moisture sensor according to the invention. As in FIG. 3, the relative humidity in the chamber was varied in steps and the signal generated by the moisture sensor was measured. In this case, the transducer used to generate this data was a 5 mm long sol-gel fiber with a 200 µm diameter. The concentration of cobalt chloride in the fiber was 3.5%. As can be seen by comparing FIG. 4 to FIG. 3, the 200 µm diameter sensor has a much faster response (i.e., within one minute) to moisture change compared with that of a 400 µm diameter fiber sensor (about 8 minutes).

Figure 5:
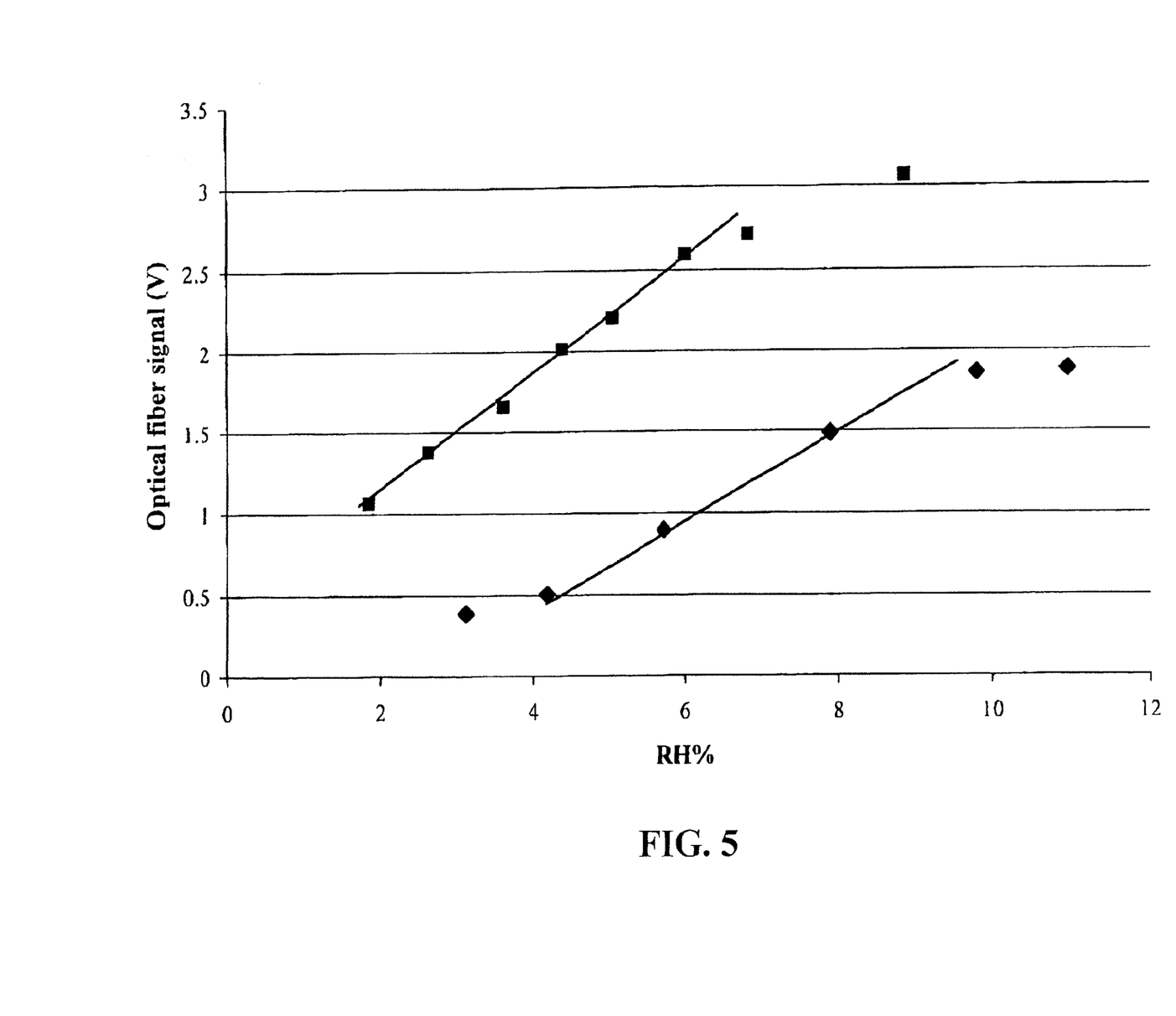
FIG. 5 shows the calibration curves for the optical fiber moisture sensors of FIGS. 3 and 4.

The calibration curves for the moisture sensors of FIGS. 3 and 4 are shown in FIG. 5. For the 2% $CoCl_2$ doped sol-gel fiber sensor (i.e., the sensor of FIG. 3) the sensor signal (■) is approximately linear within the relative humidity range of 2% to 7%. For the 3.5% $CoCl_2$ doped sol-gel fiber sensor (i.e., the sensor of FIG. 4), the sensor signal (♦) is approximately linear with relative humidity from 4% to 9.5%. As can be seen from FIG. 5, the detection limit of the 200 µm sol-gel fiber sensor is higher than that of the 400 µm sensor because of a higher $CoCl_2$ content in the transducer of this sensor.

Certain characteristics of the moisture sensors according to the invention should be noted. First, moisture sensors according to the invention are highly sensitive compared to evanescent wave absorption-based (i.e., active cladding type) moisture sensors. Evanescent wave absorption based moisture sensors, for example, as disclosed in Hypszer et al., "Fiber Optic Technique for Relative Humidity Sensors", SPIE, 3054, 145 (1997), give detectable signals only when the relative humidity is higher than 60%. In order to verify these findings, an evanescent wave absorption based moisture sensor was constructed and the result detection limits were found to be similar to that obtained by Hypszer et al. In contrast, as set forth above, moisture sensors according to the invention can detect moisture contents as low as 2% relative humidity.

A second characteristic is that the sensing process is reversible. For example, the sensors can be reused upon drying (i.e., removal of the moisture from) the transducer. Drying can be accomplished, for example, by heating the transducer and/or by purging dry gas through the chamber housing the transducer. The sensors can also be regenerated periodically and used for continuous monitoring.

A third advantage of these moisture sensors is that the $CoCl_2$ dopant is firmly trapped in the sol-gel fiber. Therefore, the sensor can be used for high humidity detection without the possibility of re-distribution of the sensing material in the transducer. The re-distribution of sensing material can be a problem in sensors in which water-soluble sensing material is coated on the surface of the micro pore structure of a porous glass or when the sensing material is trapped in water-soluble polymer film.

The detection limit of a moisture sensor made according to the method of the invention can be further improved by adjusting the content of $CoCl_2$ in the sol-gel fiber. Also, the response time of moisture sensors according to the invention is dependent on the diameter and the porosity of the sol-gel fiber. Therefore, the response time of the sensor can be optimized for a given application by adjusting these variables.

EXAMPLE 2

Ammonia Sensor

Ammonia is known to form a complex with $Cu^{2+}$ ions. It is also known that ammonia is a stronger coordinating ligand to cupric ions than water molecules. Therefore, the replacement reaction:

$$Cu(H_2O)_4^{2+} + 4NH_3 \rightarrow Cu(NH_3)_4^{2+} + 4H_2O$$

can occur either in aqueous solution or through a gas-solid reaction. The cupric water complex has a green color while the cupric ammonia complex is blue colored. Therefore, through detecting the light absorption signal of the formed cupric ammonia complex, ammonia in aqueous solution or in gas phase can be detected. This property can therefore be used for constructing an ammonia sensor using an active sol-gel fiber core.

Accordingly, copper chloride ($CuCl_2$) was dissolved in water and the resulting solution was used in the hydrolysis of TMOS. The resulting clear silicic acid solution was filled into a tube and gelatinized. The resulting copper chloride doped sol-gel fiber was pushed out of the tube and air-dried.

An optical fiber ammonia sensor was constructed using the cupric chloride doped sol-gel fiber as the transducer. A green LED having an emission peak at 550 nm with a 50 nm bandwidth was used as a light source and a charge coupled device (CCD) was used as a light detector. A quartz optical fiber was used to send light from the light source to the transducer and another quartz fiber for guiding light from the transducer to the light detector.

The transducer was sealed in a small plastic chamber having two openings for coupling of two quartz fibers to the transducer and having an inlet and an outlet port for flowing the sample fluid in and out. The absorbance signal of light from the green LED was monitored for ammonia detection.

Figure 6:
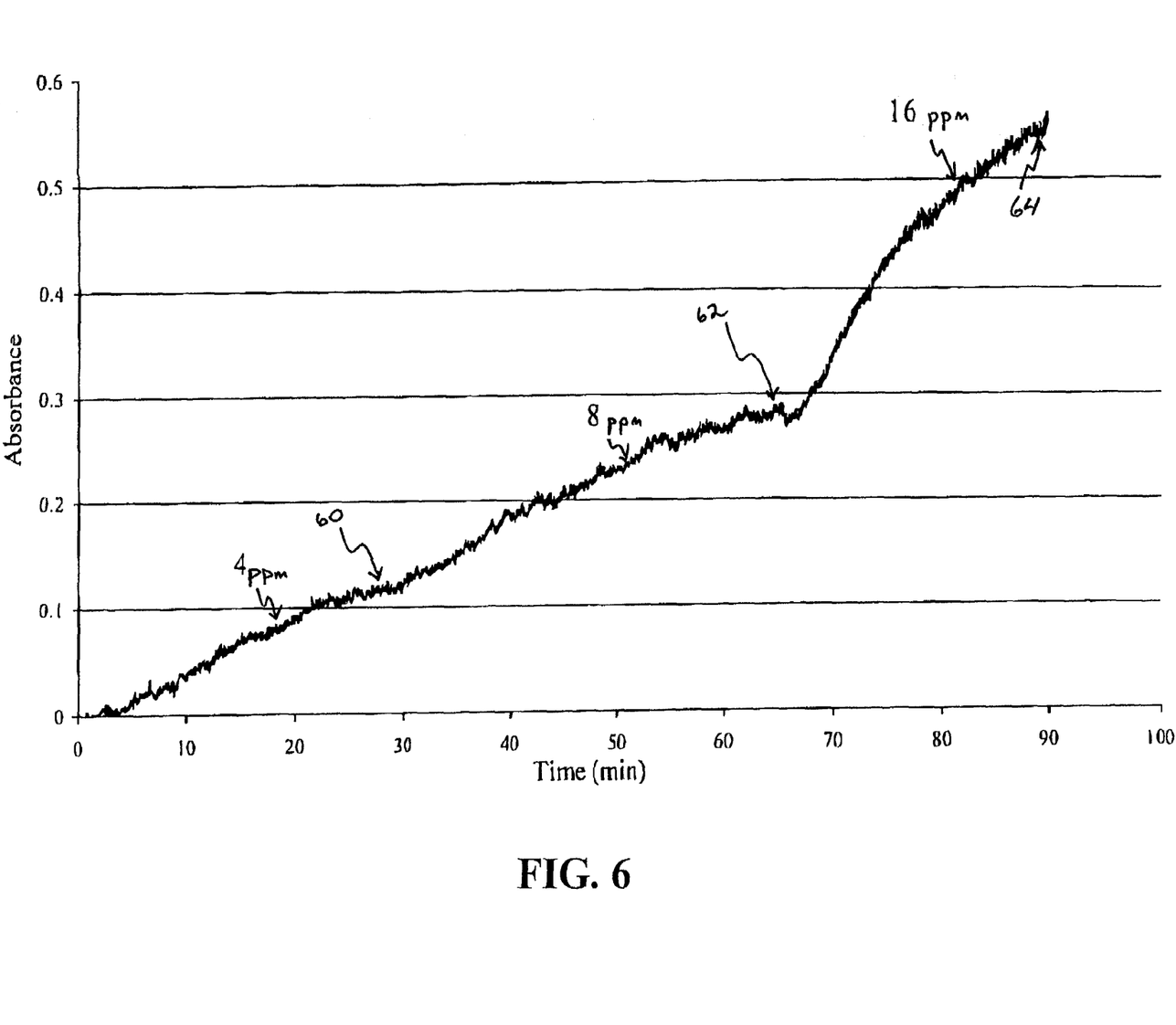
FIG. 6 shows absorbance as a function of time for an ammonia sensor for detecting ammonia in water according to the invention.

Ammonia in water was detected by pumping ammonia aqueous solution through the sensor. FIG. 6 shows the results for a sensor having a 1 cm. length. In FIG. 6, absorbance is plotted as a function of time for three different concentrations (4 ppm, 8 ppm and 16 ppm) of $NH_3$ in aqueous solution. At 4 ppm $NH_3$, the absorbance value plateaus at a value of approximately 0.12. This point is indicated by reference numeral 60. This plateau occurs at a time of about 30 minutes. When the $NH_3$ concentration is increased to 8 ppm, the absorbance value plateaus at a value of approximately 0.28. This point is indicated by reference numeral 62. This plateau occurs at a time of about 35 minutes after the $NH_3$ concentration is increased to 8 ppm (i.e., at about 65 min.). When the $NH_3$ concentration is increased to 16 ppm, the absorbance value plateaus at a value of approximately 0.56. This point is indicated by reference numeral 64. This plateau occurs at a time of about 30 minutes after the $NH_3$ concentration is increased to 16 ppm (i.e. at about 90 min.). In this experiment, a 400 μm diameter sol-gel fiber having a doping concentration of 8% $CuCl_2$ was used as the transducer.

Figure 7:
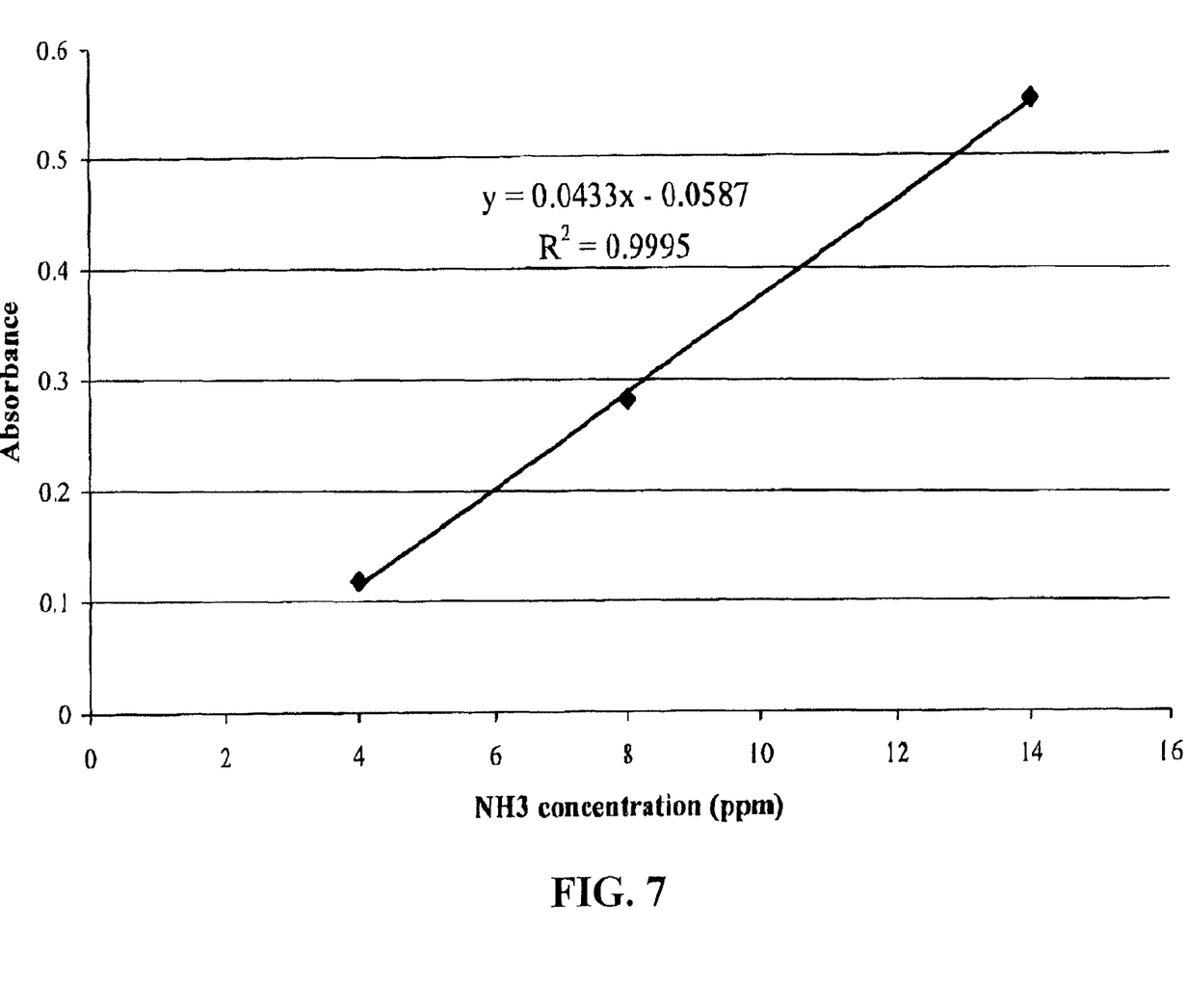
FIG. 7 shows the calibration curve for the ammonia sensor of FIG. 6.

FIG. 7 shows the absorption signal as a function of the concentration of ammonia in aqueous solution in the test range from 4 ppm to 16 ppm for the data from FIG. 6. The absorption of the cupric ammonia complex was monitored. As can be seen from FIG. 7, the absorption signal has an approximately linear relationship with respect to the concentration of ammonia in aqueous solution over the range tested. A linear fit of the data yielded the equation:

$$y = 0.0433x - 0.0587$$

wherein the variable y is the absorbance and the variable x is the $NH_3$ concentration in ppm. The $R^2$ value was 0.9995.

The concentration of ammonia in a gas phase was also detected using a $CuCl_2$-doped optical fiber sensor according to the invention. For this experiment, a sol-gel fiber having a length of 1 cm and a diameter of 400 μm and doped with 3% $CuCl_2$ was used as a transducer. Approximately 50 ml of ammonia aqueous solution was prepared in a one liter plastic bottle. The head-space gas, which equilibrates with the ammonia in aqueous solution, was used as sample gas. Air was flowed through the bottle and carried the sample gas containing ammonia into the chamber housing the transducer.

Figure 8:
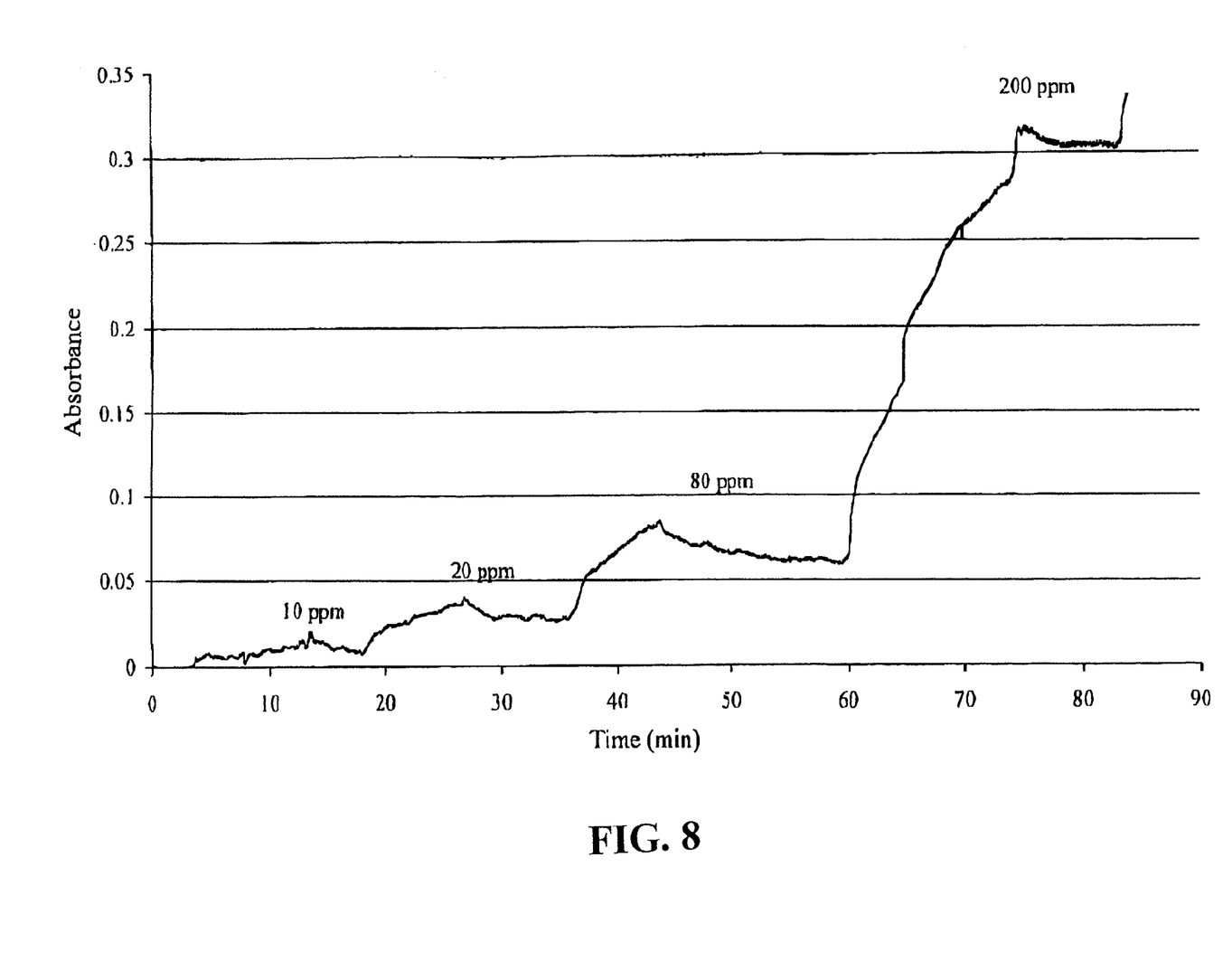
FIG. 8 shows absorbance as a function of time for an ammonia sensor for detecting ammonia in head space gas equilibrated with ammonia solution according to the invention.

The test result are shown in FIG. 8. FIG. 8 shows absorbance as a function of time for four different concentrations of ammonia in a gas phase. As can be seen from FIG. 8, trace ammonia in a head space gas equilibrated with a 10 ppm ammonia aqueous solution can be detected with the sensor. Ammonia in head-space gas equilibrated with 20 ppm, 80 ppm and 200 ppm ammonia solution were also measured.

The ammonia sensor described above cannot easily be reused since the ammonia bonds with cupric ions and cannot be easily removed. However, the sensor can be reset by flowing a diluted hydrochloric acid solution through the transducer after each detection.

These and other modifications and variations to the present invention may be practiced by those of ordinary skill in the art, without departing from the spirit and scope of the present invention. Furthermore, those of ordinary skill in the art will appreciate that the foregoing description is by way of example only, and is not intended to limit the invention.

What is claimed is:

1. A method for making a porous sol-gel fiber, the method comprising steps of:
   hydrolyzing a silicate ester with water using a catalyst to form a hydrolyzed solution;
   transferring the hydrolyzed solution into the cavity of a mold;
   allowing the hydrolyzed solution to gelatinize to form a sol-gel fiber;
   removing the sol-gel fiber from the mold; and
   drying the sol-gel fiber.

2. The method of claim 1, wherein the silicate ester is tetramethyl orthosilicate or tetraethyl orthosilicate.

3. The method of claim 1, wherein the volume ratio of the silicate ester to water is 2 or less.

4. The method of claim 1, wherein the catalyst is a mineral acid catalyst.

5. The method of claim 1, wherein the mold cavity is a tubular cavity.

6. The method of claim 1, wherein the hydrolyzed solution is allowed to gelatinize for at least two days.

7. The method of claim 1, wherein the sol-gel fiber is removed from the mold by injecting a fluid into the mold.

8. The method of claim 1, wherein the drying step comprises allowing the sol-gel fiber to air dry.

9. The method of claim 1, further comprising a step of incorporating a sensing material into the sol-gel fiber.

10. The method of claim 9, wherein the sensing material is added to the water used for the hydrolysis.

11. The method of claim 9, wherein the sensing material is added to the hydrolyzed solution.

12. The method of claim 9, wherein the sensing material is absorbed into the sol-gel fiber by dipping the sol-gel fiber into a solution comprising the sensing material.

13. The method of claim 9, wherein the sensing material is optically changeable in the presence of water.

14. The method of claim 9, wherein the sensing material is optically changeable in the presence of ammonia.

15. The method of claim 9, wherein the sensing material is $CoCl_2$ or $CuCl_2$.

16. A porous sol gel fiber made by the method of claim 1.

17. A porous sol gel fiber made by the method of claim 9.

18. The porous sol-gel fiber of claim 17, further comprising a cladding material disposed on the fiber.

19. The porous sol-gel fiber of claim 17, wherein the sensing material is $CoCl_2$ or $CuCl_2$.

20. A method for constructing an optical fiber sensor, the method comprising steps of:
   hydrolyzing a silicate ester with water using a catalyst to form a hydrolyzed solution;
   transferring the hydrolyzed solution into the cavity of a mold;
   allowing the hydrolyzed solution to gelatinize to form a sol-gel fiber;
   removing the sol-gel fiber from the mold;
   drying the sol-gel fiber, to produce a porous sol-gel fiber; and
   positioning the porous sol-gel fiber between a light source and a light detector.

21. The method of claim 20, further comprising a step of incorporating a sensing material into the sol-gel fiber.

22. The method of claim 21 wherein the sensing material is optically changeable in the presence of moisture or ammonia.

23. The method of claim 20, wherein the diameter of the air dried sol-gel fiber is about 500 μm or less.

24. The method of claim 20, wherein the length of the air dried sol-gel fiber is at least 1 mm.

25. The method of claim 21, wherein the sensing material is optically changeable in the presence of water.

26. An optical fiber sensor comprising:
   a light source;
   a light detector; and
   a transducer;
   wherein the transducer comprises the porous sol-gel fiber of claim 17 and wherein light from the light source passes through the transducer and impinges on the light detector.

27. The optical fiber sensor of claim 26, further comprising a lens positioned between the light source and the transducer wherein light from the light source is focused by the lens before passing through the transducer.

28. The optical fiber sensor of claim 26, further comprising a first optical fiber positioned between the lens and the transducer, wherein the first optical fiber is optically coupled to a first end of the transducer such that light from the light source passes through the first optical fiber before passing through the transducer.

29. The optical fiber sensor of claim 26, further comprising a second optical fiber positioned between the transducer and the light detector, wherein the second optical fiber is optically coupled to a second end of the transducer such that light passing through the transducer passes through the second optical fiber before impinging on the light detector.

30. The optical fiber sensor of claim 26, further comprising a data acquisition system in communication with the light detector.

31. The optical fiber sensor of claim 30, wherein the data acquisition system comprises a computer for analyzing data generated by the light detector.

32. The optical fiber sensor of claim 26, wherein the light source is: a line source; a band source; or a continuous light source coupled with a monochromator or band-pass filter.

33. The optical fiber sensor of claim 26, wherein the light detector is a photodiode, a photomultiplier tube or a charge coupled detector.

34. The optical fiber sensor of claim 26, wherein the transducer is positioned inside a chamber.

35. The optical fiber sensor of claim 34, wherein the chamber comprises an inlet and an outlet such that a fluid flowing into the chamber through the inlet contacts the transducer and exits the chamber through the outlet.

36. The optical fiber sensor of claim 35, further comprising:
   a first optical fiber which passes through a first opening in the chamber and is optically coupled to a first end of the transducer inside the chamber such that light from the light source passes through the first optical fiber before passing through the transducer; and
   a second optical fiber which is optically coupled to a second end of the transducer inside the chamber and which passes through a second opening in the chamber such that light passing through the transducer passes through the second optical fiber before impinging on the light detector.

37. A method for determining the presence or concentration of an analyte in a sample fluid using the sensor of claim 26, the method comprising steps of:
   contacting the transducer with the sample fluid; and
   monitoring the signal from the light detector while directing light from the light source through the transducer.

38. The method of claim 37, wherein the contacting step comprises positioning the transducer in the sample fluid.

39. The method of claim 37, wherein the dopant in the sol-gel fiber interacts with the analyte.

40. The method of claim 39, wherein the monitoring step comprises monitoring the absorbance of the analyte.

41. The method of claim 39, wherein the dopant forms a complex with the analyte.

42. The method of claim 41, wherein the monitoring step comprises monitoring absorbance of the complex or fluorescent emissions of the complex.

43. The method of claim 37, wherein the signal from the light detector is compared to a calibration curve to determine the amount of analyte in the sample.

44. The method of claim 43, wherein the calibration curve is generated by a process comprising steps of:
   contacting the transducer with a first fluid sample having a known concentration of analyte;
   monitoring the signal from the light detector while directing light through the transducer to generate a first data point;
   contacting the transducer with a second fluid sample having a known concentration of analyte different than the first fluid sample;
   monitoring the signal from the light detector while directing light through the transducer to generate a second data point;
   optionally generating additional data points using additional fluid samples having known concentrations of the analyte; and
   fitting a curve to the data points to generate the calibration curve.

45. The method of claim 37, wherein the analyte is ammonia and the sensing material is $CuCl_2$, the method further comprising a step of exposing the sol-gel fiber to a solution comprising hydrochloric acid after the monitoring step to reset the sensor.

46. An optical fiber sensor comprising:
   a light detector; and
   a transducer in optical communication with the light detector such that light generated within the transducer impinges on the light detector;
   wherein the transducer comprises the porous sol-gel fiber of claim 17.

47. The optical fiber sensor of claim 46, further comprising a light source, wherein light from the light source impinges on a surface of the transducer.

48. A method for determining the presence or concentration of an analyte in a sample fluid using the sensor of claim 46, the method comprising steps of:
   contacting the transducer with the sample fluid; and
   monitoring the signal from the light detector.

49. A method for determining the presence or concentration of an analyte in a sample fluid using the sensor of claim 47, the method comprising steps of:
   contacting the transducer with the sample fluid; and
   monitoring the signal from the light detector while applying light to the surface of the transducer.

* * * * *